US00PP17412P2

(12) United States Plant Patent
Bergman

(10) Patent No.: US PP17,412 P2
(45) Date of Patent: Feb. 13, 2007

(54) ***CHRYSANTHEMUM* PLANT NAMED 'YOMISTIQUE'**

(50) Latin Name: *Chrysanthemum ×morifolium*
Varietal Denomination: Yomistique

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 13 days.

(21) Appl. No.: 11/157,439

(22) Filed: Jun. 21, 2005

(51) Int. Cl.
*A01H 5/00* (2006.01)

(52) U.S. Cl. ..... Plt./286

(58) Field of Classification Search ..... Plt./286
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Yomistique', characterized by its uniform, compact and somewhat outwardly spreading plant habit; strong and freely branching growth habit; dense and bushy appearance; dark green-colored foliage; uniform flowering response and habit; typically grown as a spray-type; very early flowering habit; small daisy-type inflorescences with elongated oblong-shaped ray florets; purple-colored ray florets with light yellow green towards the base; and excellent postproduction longevity with plants maintaining good substance and color for about four to five weeks in an interior environment.

2 Drawing Sheets

Botanical designation: *Chrysanthemum×morifolium.*
Cultivar denomination: 'Yomistique'.

BACKGROUND OF THE INVENTION

The present Invention relates to a new and distinct cultivar of *Chrysanthemum* plant, botanically known as *Chrysanthemum×morifolium* and hereinafter referred to by the name 'Yomistique'.

The new *Chrysanthemum* is a product of a planned breeding program conducted by the Inventor in Salinas, Calif. and Alva, Fla. The objective of the program is to create or discover new potted *Chrysanthemum* cultivars that are suitable for year-round production with uniform plant growth habit, good vigor and strong branching habit, numerous inflorescences, desirable inflorescence form and floret colors, fast and uniform flowering response, and good postproduction longevity.

The new *Chrysanthemum* originated from a cross-pollination made in August, 1997 in Salinas, Calif., of a proprietary selection of *Chrysanthemum×morifolium* identified as code number YB-6500, not patented, as the female, or seed, parent with a proprietary selection of *Chrysanthemum×morifolium* identified as code number YB-4714, not patented, as the male, or pollen, parent. The new *Chrysanthemum* was discovered and selected by the Inventor as a single flowering plant within the progeny of the stated cross-pollination grown in a controlled environment in Alva, Fla. in December, 1998. The selection of this plant was based on its uniform plant growth habit, good vigor and strong branching habit, desirable inflorescence form and floret colors, fast and uniform flowering response, and good postproduction longevity.

Asexual reproduction of the new *Chrysanthemum* by vegetative tip cuttings was first conducted in Avla, Fla. in March, 1999. Asexual reproduction by cuttings has shown that the unique features of this new *Chrysanthemum* are stable and reproduced true to type in successive generations.

SUMMARY OF THE INVENTION

The cultivar Yomistique has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Yomistique'. These characteristics in combination distinguish 'Yomistique' as a new and distinct *Chrysanthemum:*

1. Uniform, compact and somewhat outwardly spreading plant habit.
2. Strong and freely branching growth habit; dense and bushy appearance.
3. Dark green-colored foliage.
4. Uniform flowering response and habit.
5. Typically grown as a spray-type.
6. Very early flowering, six week response time.
7. Small daisy-type inflorescences with elongated oblong-shaped ray florets.
8. Purple-colored ray florets with light yellow green towards the base forming a halo around the disc.
9. Excellent postproduction longevity with plants maintaining good substance and color for about four to five weeks in an interior environment.

Plants of the new *Chrysanthemum* can be compared to plants of the female parent selection. Plants of the new *Chrysanthemum* differ from plants of the female parent selection primarily in ray floret coloration as plants of the female parent selection have pink-colored ray florets. In addition, plants of the new *Chrysanthemum* have better postproduction longevity than plants of the female parent selection.

Plants of the new *Chrysanthemum* can be compared to plants of the male parent selection. Plants of the new *Chrysanthemum* differ from plants of the male parent selection primarily in ray floret coloration as plants of the male parent selection have pink-colored ray florets. In addition, plants of the new *Chrysanthemum* flower about two weeks earlier than plants of the male parent selection.

Plants of the new *Chrysanthemum* can be compared to plants of the cultivar Yomarcelle, disclosed in U.S. Plant Pat. No. 13,034. In side-by-side comparisons conducted in Alva, Fla., plants of the new *Chrysanthemum* differed from plants of the cultivar Yomarcelle in the following characteristics:

1. Plants of the new *Chrysanthemum* had larger inflorescences than plants of the cultivar Yomarcelle.
2. Plants of the new *Chrysanthemum* and the cultivar Yomarcelle differed in ray floret coloration.

BRIEF DESCRIPTION OF THE PHOTOGRAPHS

The accompanying colored photographs illustrate the overall appearance of the new *Chrysanthemum* showing the colors as true as it is reasonably possible to obtain in colored reproductions of this type. Colors in the photographs may differ from the color values cited in the detailed botanical description which accurately describe the colors of the new *Chrysanthemum.*

The photograph on the first sheet comprises a side perspective view of typical flowering plants of 'Yomistique' grown as spray-types.

The photograph on the second sheet comprises a close-up view of typical inflorescences of 'Yomistique' grown as spray-types.

DETAILED BOTANICAL DESCRIPTION

In the following description, color references are made to The Royal Horticultural Society Colour Chart, 1995 Edition, except where general terms of ordinary dictionary significance are used. The aforementioned photographs, following observations and measurements describe plants grown and flowered during the spring in Salinas, Calif., in a fiberglass-covered greenhouse and under conditions which approximate those generally used in commercial potted *Chrysanthemum* production. During the production of these plants, the following conditions were measured: day temperatures, 21 to 27° C.; night temperatures, 17 to 19° C.; and light levels, 5,000 to 6,000 foot-candles. Four unrooted cuttings were directly stuck in 15-cm containers, exposed to long day/short night conditions, and pinched once about two weeks later. At the time of the pinch, the photoinductive short day/long night treatments were initiated. Plants used for the description were grown as spray-types. Measurements and numerical values represent averages of typical flowering plants.

Botanical classification: *Chrysanthemum×morifolium* cultivar Yomistique.

Commercial classification: Daisy-type potted *Chrysanthemum.*

Parentage:

*Female, or seed, parent.*—Proprietary selection of *Chrysanthemum×morifolium* identified as code number YB-6500, not patented.

*Male, or pollen, parent.*—Proprietary selection of *Chrysanthemum×morifolium* identified as code number YB-4714, not patented.

Propagation:

*Type.*—Terminal tip cuttings.

*Time to initiate roots.*—About four days at 21° C.

*Time to produce a rooted cutting.*—About ten days at 21° C.

*Root description.*—Fibrous; white, close to 155D, in color.

*Rooting habit.*—Freely branching; moderately dense.

Plant description:

*Appearance.*—Herbaceous daisy-type potted *Chrysanthemum* that is typically grown as a spray-type. Upright with lateral branches somewhat outwardly spreading; compact; uniformly mounded crown. Strong and freely branching growth habit; about three or four lateral branches develop after removal of terminal apex (pinching); dense and full plants.

*Plant height.*—About 20 cm.

*Plant width.*—About 32 cm.

*Lateral branches.*—Length: About 15 cm. Diameter: About 4 mm. Internode length: About 1.3 cm. Strength: Strong. Texture: Pubescent. Color: 146A.

*Foliage description.*—Arrangement: Alternate; simple. Length: About 6.8 cm. Width: About 4.2 cm. Apex: Mucronate. Base: Attenuate. Margin: Palmately lobed, sinuses between lateral lobes parallel to divergent. Texture, upper and lower surfaces: Pubescent. Color: Developing and fully expanded foliage, upper surface: More green than 147A. Developing and fully expanded foliage, lower surface: Close to 147B. Venation, upper surface: Close to 147A. Venation, lower surface: Close to 146A. Petiole length: About 1.9 cm. Petiole diameter: About 3 mm. Petiole texture, upper and lower surfaces: Pubescent. Petiole color, upper and lower surfaces: Close to 146A.

Inflorescence description:

*Appearance.*—Daisy-type inflorescence form with elongated oblong-shaped ray florets. Inflorescences borne on terminals above foliage. Disk and ray florets develop acropetally on a capitulum. Inflorescences slightly fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Uniform and early flowering habit; plants exposed to two weeks of long day/short night conditions followed by photoinductive short day/long night conditions flower about six weeks later; very early flowering.

*Postproduction longevity.*—Inflorescences maintain good color and substance for about four to five weeks in an interior environment.

*Quantity of inflorescences.*—Grown as a spray-type, about five per lateral branch.

*Inflorescence bud.*—Height: About 4 mm. Diameter: About 3 mm. Shape: Oblate. Color: 146A to 147A.

*Inflorescence diameter.*—Small, about 3.3 cm.

*Inflorescence height.*—About 1 cm.

*Diameter of disc.*—About 1.8 cm.

*Receptacle diameter.*—About 4 mm.

*Receptacle height.*—About 5 mm.

*Ray florets.*—Length: About 1.6 cm. Width: About 5 mm. Corolla tube length: About 3 mm. Shape: Elongated oblong. Apex: Emarginate. Base: Fused into a corolla tube. Margin: Entire. Orientation: Initially upright to eventually perpendicular to the peduncle. Texture, upper and lower surfaces: Smooth, glabrous; satiny. Number of ray florets per inflorescence: About 22 arranged in a single whorl. Color: When opening, upper surface: Close to 77A. When opening, lower surface: Slightly lighter than 77A. Fully opened, upper surface: Close to 77A; towards the base, close to 154D. Fully opened, lower surface: Close to 77A to 77B; towards the base, close to 154C to 154D.

*Disc florets.*—Arrangement: Massed at center of receptacle. Length: About 6 mm. Diameter, apex: About 2 mm. Diameter, base: About 1 mm. Shape: Tubular; elongated. Apex: Five-pointed. Number of disc florets per inflorescence: About 122. Color: Immature: Close to 144A. Mature, apex: Close to 9A. Mature, mid-section: Close to 144A. Mature, base: Close to 155D.

*Phyllaries.*—Quantity per inflorescence: About 24 arranged in about three whorls. Length: About 6 mm. Width: About 3 mm. Shape: Lanceolate. Apex: Acute. Base: Truncate. Margin: Entire. Texture, upper surface: Waxy, smooth. Texture, lower surface: Pubescent. Color, upper surface: Close to 146A. Color, lower surface: 146A to 147A.

*Peduncles.*—Length, terminal peduncle: About 2.8 cm. Length, fourth peduncle: About 3.6 cm. Diameter: About 2 mm. Strength: Strong. Texture: Pubescent. Angle: About 30° from vertical. Color: Close to 146A.

*Reproductive organs.*—Androecium: Present on disc florets only. Anther length: Less than 1 mm. Anther color: Close to 23A. Pollen amount: None observed. Gynoecium: Present on both ray and disc florets. Style length: About 5 mm. Style color: Close to 154A. Stigma color: Close to 13A.

*Seed/fruit.*—Seed and fruit production has not been observed.

Disease/pest resistance: Resistance to pathogens and pests common to *Chrysanthemums* has not been observed on plants grown under commercial greenhouse conditions.

It is claimed:

1. A new and distinct cultivar of *Chrysanthemum* plant named 'Yomistique', as illustrated and described.

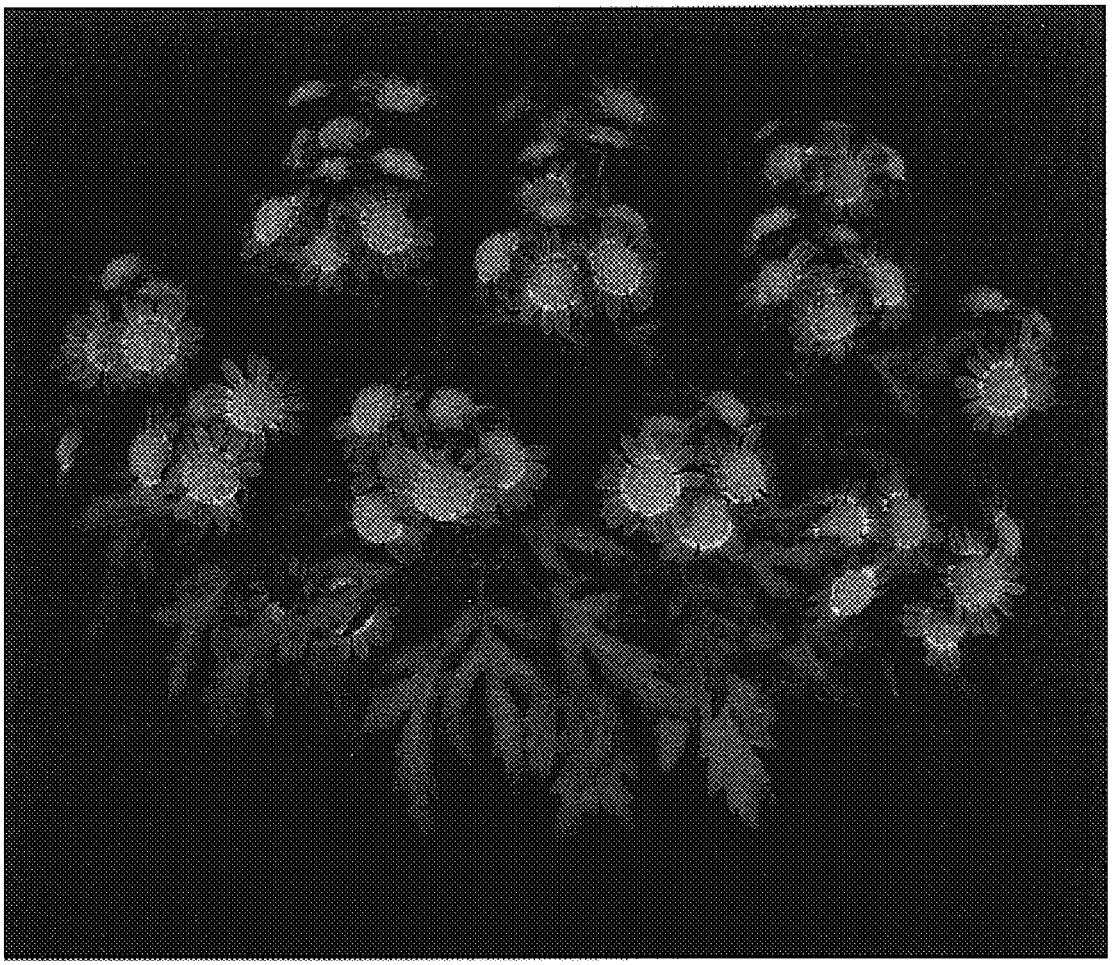

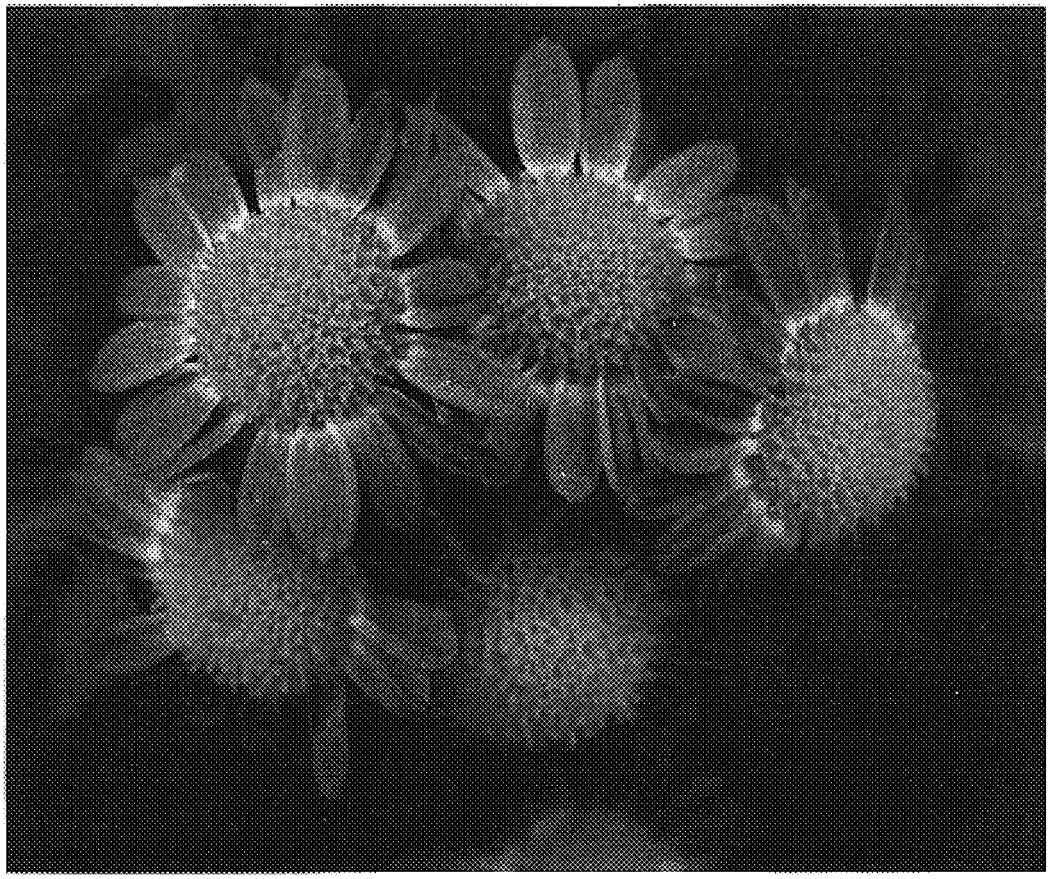

* * * * *